US011918731B2

(12) United States Patent
Porter et al.

(10) Patent No.: US 11,918,731 B2
(45) Date of Patent: Mar. 5, 2024

(54) AEROSOL DELIVERY SYSTEM AND METHOD

(71) Applicant: Stamford Devices Ltd., Dangan (IE)

(72) Inventors: Shaun Porter, Dangan (IE); Louise Sweeney, Dangan (IE); Ronan MacLoughlin, Dangan (IE); Jim Fink, San Mateo, CA (US); Aidan Duffy, Dangan (IE); Claire Lillis, Dangan (IE); Conor Duffy, Dangan (IE); Fran Keating, Dangan (IE)

(73) Assignee: Stamford Devices Ltd., Dangan (IE)

( * ) Notice: Subject to any disclaimer, the term of this patent is extended or adjusted under 35 U.S.C. 154(b) by 40 days.

(21) Appl. No.: 17/333,694

(22) Filed: May 28, 2021

(65) Prior Publication Data

US 2021/0283345 A1    Sep. 16, 2021

Related U.S. Application Data

(62) Division of application No. 15/933,219, filed on Mar. 22, 2018, now Pat. No. 11,027,077.
(Continued)

(51) Int. Cl.
*A61M 11/00*    (2006.01)
*A61M 15/00*    (2006.01)
(Continued)

(52) U.S. Cl.
CPC ......... *A61M 11/005* (2013.01); *A61M 11/001* (2014.02); *A61M 15/0085* (2013.01);
(Continued)

(58) Field of Classification Search
CPC .............. A61M 11/005; A61M 11/001; A61M 15/0085; A61M 15/08; A61M 16/0003;
(Continued)

(56) References Cited

U.S. PATENT DOCUMENTS

2003/0140921 A1* 7/2003 Smith ............... A61M 15/0031
128/200.14
2003/0205229 A1* 11/2003 Crockford ......... A61M 15/0086
128/200.23
(Continued)

FOREIGN PATENT DOCUMENTS

CN    101146517 A    9/2013
CN    103415398 A    8/2016
(Continued)

OTHER PUBLICATIONS

Examination Report for EP 18 714 745.9 dated May 21, 2021, all pages.
(Continued)

*Primary Examiner* — Elliot S Ruddie
(74) *Attorney, Agent, or Firm* — Kilpatrick Townsend & Stockton LLP

(57) ABSTRACT

An aerosol delivery system that includes an aerosol generator that aerosolizes a fluid for delivery to a patient as a patient inhales. The aerosol delivery system includes a pump coupled to the aerosol generator that pumps the fluid to the aerosol generator, and a breath sensor that emits a signal as the patient breathes. A controller couples to the aerosol generator, the pump, and the breath sensor. In operation, the controller receives the signal from the breath sensor, controls a flow of fluid to the aerosol generator in response to the signal, and controls the aerosol generator to start aerosolizing the fluid before the patient inhales.

19 Claims, 10 Drawing Sheets

Related U.S. Application Data

(60) Provisional application No. 62/475,603, filed on Mar. 23, 2017, provisional application No. 62/475,618, filed on Mar. 23, 2017, provisional application No. 62/475,635, filed on Mar. 23, 2017.

(51) Int. Cl.

| | |
|---|---|
| *A61M 15/08* | (2006.01) |
| *A61M 16/00* | (2006.01) |
| *A61M 16/04* | (2006.01) |
| *A61M 16/06* | (2006.01) |
| *A61M 16/08* | (2006.01) |
| *A61M 16/14* | (2006.01) |
| *A61M 16/16* | (2006.01) |
| *B05B 12/08* | (2006.01) |
| *B05B 17/00* | (2006.01) |

(52) U.S. Cl.
CPC ........ *A61M 15/08* (2013.01); *A61M 16/0003* (2014.02); *A61M 16/022* (2017.08); *A61M 16/026* (2017.08); *A61M 16/0465* (2013.01); *A61M 16/0488* (2013.01); *A61M 16/0666* (2013.01); *A61M 16/0672* (2014.02); *A61M 16/0816* (2013.01); *A61M 16/14* (2013.01); *B05B 17/0646* (2013.01); *A61M 2016/0018* (2013.01); *A61M 2016/0021* (2013.01); *A61M 2016/0027* (2013.01); *A61M 2016/0033* (2013.01); *A61M 2016/0039* (2013.01); *A61M 2016/0042* (2013.01); *A61M 16/04* (2013.01); *A61M 16/16* (2013.01); *A61M 2202/0488* (2013.01); *A61M 2205/17* (2013.01); *A61M 2205/3303* (2013.01); *A61M 2205/332* (2013.01); *A61M 2205/3327* (2013.01); *A61M 2205/3334* (2013.01); *A61M 2205/3368* (2013.01); *A61M 2205/3375* (2013.01); *A61M 2205/3569* (2013.01); *A61M 2205/3592* (2013.01); *A61M 2205/505* (2013.01); *A61M 2209/045* (2013.01); *A61M 2209/084* (2013.01); *A61M 2230/40* (2013.01); *A61M 2230/432* (2013.01); *A61M 2230/50* (2013.01); *A61M 2230/63* (2013.01); *A61M 2240/00* (2013.01); *B05B 12/08* (2013.01)

(58) Field of Classification Search
CPC .............. A61M 16/022; A61M 16/026; A61M 16/0465; A61M 16/0488; A61M 16/0666; A61M 16/0672; A61M 16/0816; A61M 16/14; A61M 16/04; A61M 16/16; A61M 2016/0018; A61M 2016/0021; A61M 2016/0027; A61M 2016/0033; A61M 2016/0039; A61M 2016/0042; A61M 2202/0488; A61M 2205/17; A61M 2205/3303; A61M 2205/332; A61M 2205/3327; A61M 2205/3334; A61M 2205/3368; A61M 2205/3375; A61M 2205/3569; A61M 2205/3592; A61M 2205/505; A61M 2209/045; A61M 2209/084; A61M 2230/40; A61M 2230/432; A61M 2230/50; A61M 2230/63; A61M 2240/00; A61M 16/12; A61M 2202/0208; A61M 2230/42; A61M 2230/60; A61M 2230/65; B05B 17/06–0684; B05B 12/08

See application file for complete search history.

(56) References Cited

U.S. PATENT DOCUMENTS

| | | |
|---|---|---|
| 2005/0217666 A1 | 10/2005 | Fink et al. |
| 2009/0134235 A1 | 5/2009 | Ivri |
| 2009/0241948 A1* | 10/2009 | Clancy .............. A61M 15/0085 128/203.14 |
| 2012/0125334 A1 | 5/2012 | Korneff et al. |
| 2015/0165146 A1 | 6/2015 | Bowman et al. |
| 2016/0130715 A1 | 5/2016 | Xu |
| 2018/0272081 A1 | 9/2018 | Porter et al. |

FOREIGN PATENT DOCUMENTS

| | | |
|---|---|---|
| CN | 103415398 B | 8/2016 |
| CN | 104321103 B | 4/2017 |
| EP | 1066850 A1 | 1/2001 |
| JP | 2010-540526 A | 12/2010 |
| JP | 2014-506172 A | 3/2014 |
| JP | 2016-535643 A | 11/2016 |
| WO | 01-19437 A1 | 3/2001 |
| WO | 2012092163 A1 | 7/2012 |
| WO | 2013160129 A1 | 10/2013 |
| WO | 2015-196379 A1 | 12/2015 |
| WO | 2016-028525 A1 | 2/2016 |

OTHER PUBLICATIONS

International Search Report and Written Opinion for PCT/EP2018/057561 dated May 22, 2018, all pages.
Notice of Publication No. CN 110650764 dated Jan. 3, 2020 for Chinese Application No. 201880033710.0, all pages . . . This publication is in the Chinese language. The Applicant is not in possession of an English translation.
Notice of Publication No. JP 2020-511280 dated Apr. 16, 2020 for Japan Application No. 2019- 552528, all pages . . . This publication is in the Japanese language. The Applicant is not in possession of an English translation.
Third Office Action for Chinese Patent Appln No. 201880033710.0 dated Apr. 27, 2022, 5 pages.
Decision of Rejection for Japanese Patent Appln No. 2019-552528 dated Jun. 28, 2022, 2 pages.
First Office Action for CN 201880033710.0 dated May 7, 2021, all pages.
Office Action for CN 201880033710 dated Sep. 1, 2022, 9 pages.
European Search Report for EP 22179837 dated Oct. 13, 2022, 5 pages.
Second Office Action for Chinese Appln No. 201880033710.0 dated Nov. 4, 2021, all pages.
Office Action for Japanese Appln No. 2019-552528 dated Dec. 3, 2021, all pages.
Office Action dated Aug. 4, 2023 for Japanese Application 2022-173302, 5 pages. Applicant does not possess English translation of Office Acton.
Office Action for Japanese Application No. 2022-173302 dated Nov. 21, 2023, all pages.

* cited by examiner

AEROSOL DELIVERY SYSTEM AND METHOD

CROSS REFERENCE TO RELATED APPLICATIONS

This application is a divisional application of U.S. patent application Ser. No. 15/933,219, filed Mar. 22, 2018, entitled Aerosol Delivery System and Method, which claims priority to U.S. Application No. 62/475,618, filed Mar. 23, 2017, entitled Retrofit Aerosol Delivery System and Method, U.S. Application No. 62/475,635, filed Mar. 23, 2017, entitled Aerosol Delivery Device, and U.S. Application No. 62/475,603, filed Mar. 23, 2017, entitled Aerosol Delivery System and Method, the entire contents of which are incorporated by reference herein.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

There are many types of respiratory diseases that can affect the ability of patients to breathe normally. These diseases may range from a common cold to cystic fibrosis. Modern medicine treats these diseases in a variety of ways including oral medication, inhalers, nebulizers, etc. A nebulizer is a device that changes fluid (i.e., medicament) into an aerosol for delivery to a patient through breathing. The patient may receive the aerosol through the mouth, nose, and/or a tracheotomy (i.e., a surgically made cut in the throat). However, a nebulizer may not effectively treat a respiratory disease if the aerosol droplets are large and/or the aerosol formation is not properly timed with a patient's breathing cycle.

SUMMARY OF THE INVENTION

The present disclosure is directed to various embodiments of aerosol delivery systems. In some embodiments, the aerosol delivery system includes an aerosol generator that aerosolizes a fluid for delivery to a patient as a patient inhales. The aerosol delivery system includes a pump coupled to the aerosol generator that pumps the fluid to the aerosol generator, and a breath sensor that emits a signal as the patient breathes. A controller couples to the aerosol generator, the pump, and the breath sensor. In operation, the controller receives the signal from the breath sensor, controls a flow of fluid to the aerosol generator in response to the signal, and controls the aerosol generator to start aerosolizing the fluid before the patient inhales.

In some embodiments, the aerosol delivery system includes an aerosol generator that aerosolizes a fluid for delivery to a patient as a patient inhales. A pump couples to the aerosol generator that pumps the fluid to the aerosol generator, and a flow sensor configured to sense changes in fluid flow as a patient inhales. A controller couples to the aerosol generator, the pump, and the flow sensor. In operation, the controller receives the signal from the flow sensor, controls a flow of fluid to the aerosol generator in response to the signal, and controls the aerosol generator to start aerosolizing the fluid.

An aspect of the disclosure includes a method of providing aerosolized fluid to a patient. The method includes detecting a breath cycle with a breath sensor and then predicting the start of inhalation. After predicting the start of inhalation, the method preloads fluid onto a vibratable member with a pump. The vibratable member is then vibrated with a piezoelectric actuator to aerosolize the fluid.

BRIEF DESCRIPTION OF THE DRAWINGS

Various features, aspects, and advantages of the present invention will be better understood when the following detailed description is read with reference to the accompanying figures in which like characters represent like parts throughout the figures, wherein.

DETAILED DESCRIPTION

One or more specific embodiments of the present invention will be described below. These embodiments are only exemplary of the present invention. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The embodiments discussed below include an aerosol delivery system capable of predicting patient inhalation in order to time production and delivery of an inhalable aerosol medicament. For example, the aerosol delivery system may predict inhalation so that the medicament can be aerosolized before inhalation. By aerosolizing the medicament on patient inhalation, the aerosol delivery system increases the amount of medication delivered to the patient per breath, enhances the effectiveness of the medication, and/or delivers the medication to a greater area within a patient's lungs (e.g., deeper into the lungs). The aerosol delivery system uses one or more breath sensors to detect inhalation by a patient. These breath sensors may detect inhalation across all ventilation modes including mandatory, assisted, and spontaneous. For example, the aerosol delivery system may use a flow sensor as the breath sensor to detect inhalation by a patient. As will be explained below, flow sensors are more effective than pressure sensors at detecting the start and stop of inhalation.

The aerosol delivery system may also increase delivery effectiveness with an aerosol generator capable of producing fine particle fractions (FPF) greater than 80% with droplets/particles having a volume median diameter (VMD) of 1 micron or less. In other words, the aerosol generator is capable of producing very fine aerosols that are easily suspended in and carried by a carrier fluid (e.g., air, O2, O2/air mixture, etc.). Finally, the aerosol delivery systems discussed below may couple to existing respiratory systems without redesigning or reengineering those systems. This enables the aerosol delivery system to be used with existing ventilators, humidifiers, continuous positive airway pressure (CPAP) machines, etc.

Figure 1:
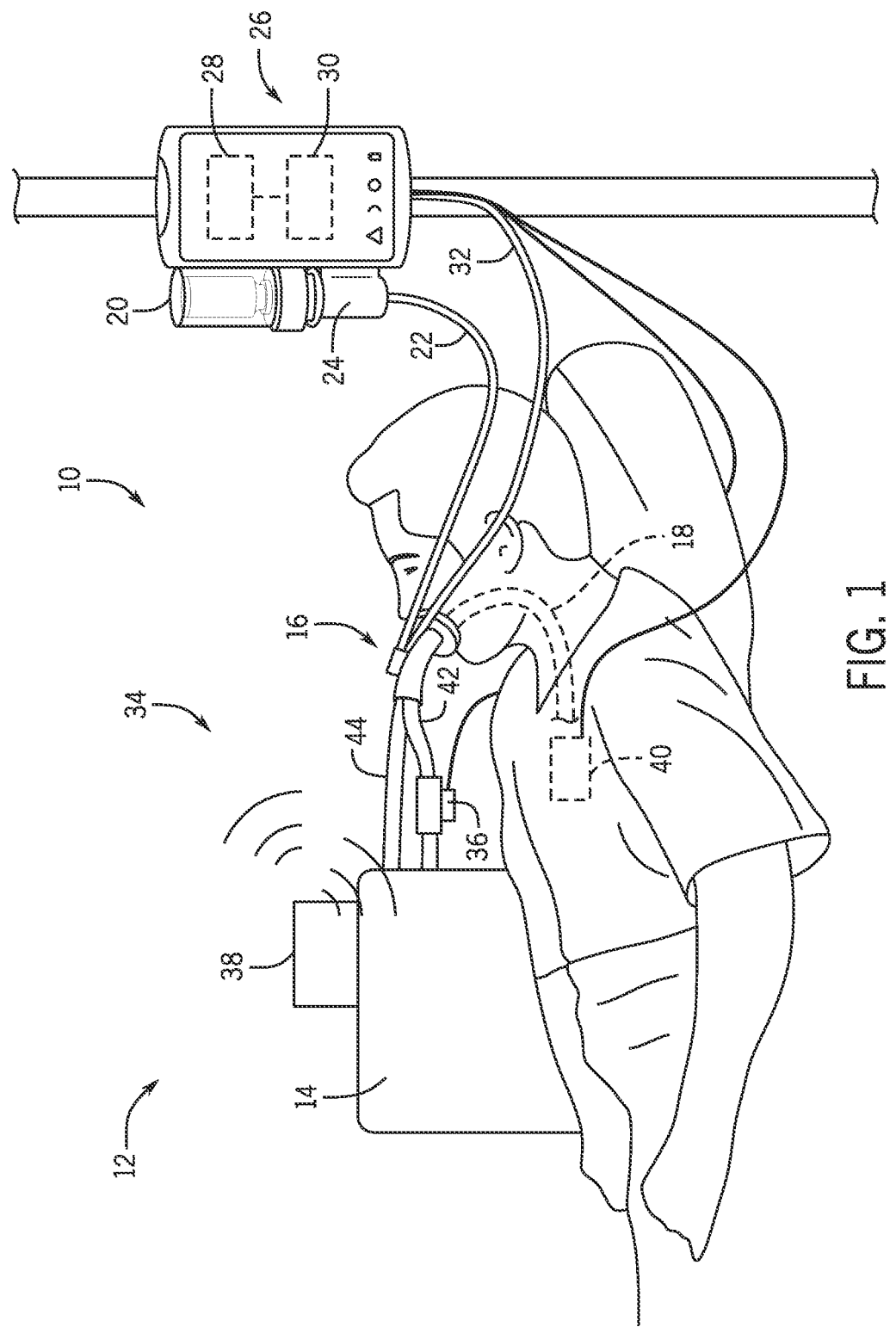
FIG. 1 is a schematic view of an embodiment of an aerosol delivery system connected to a respiratory system.

FIG. 1 is a schematic view of an embodiment of an aerosol delivery system 10 connected to a respiratory system 12. In FIG. 1, the respiratory system 12 includes a ventilator 14 capable of forcing air (e.g., air, O2, air/O2 mixture, etc.) into and withdrawing air from a patient. As will explained in detail below, the aerosol delivery system 10 is capable of connecting to a variety of existing respiratory systems 12 to provide aerosolized fluid (e.g., medicament) for patient treatments. That is, the aerosol delivery system 10 may be retrofitted to existing respiratory systems 12 (e.g., ventilators, humidifiers, continuous positive airway pressure (CPAP) machines, or combinations thereof) without redesigning or reengineering the respiratory system 12 to work with the aerosol delivery system 10.

The aerosol delivery system 10 includes an aerosol generator 16 capable of coupling to a variety of airflow devices such as endotracheal tubes 18, nasal cannula/masks, tracheostomy tubes, etc. The aerosol generator 16 receives fluid from a fluid source 20 through a fluid delivery conduit 22. The fluid source 20 (e.g., container, vial) may contain a variety of substances including medicament, surfactant, a combination thereof, etc. In operation, fluid from the fluid source 20 is pumped with a pump 24 through the fluid delivery conduit 22 to the aerosol generator 16 where the fluid is aerosolized before and/or while the patient inhales. In some embodiments, the fluid delivery conduit 22 may be primed with fluid before treatment to ensure rapid delivery (e.g., preloading fluid in aerosol generator 16). The pump 24 is controlled with a controller 26, which times delivery and dosage of the fluid.

The controller 26 includes one or more processors 28 that execute instructions stored on one or more memory 30 to drive operation of the pump 24 and the aerosol generator 16. For example, the memory 30 may include instructions that indicate the amount of fluid to be pumped to the aerosol generator 16 in each dose for each actuation of the aerosol generator 16, how much fluid is to be pumped over a specific period of time or times, etc. The stored instructions may be based on a size of the patient, age of the patient, sex of the patient, type of medicament, fluid additives, desired amount of aerosol, etc. The memory 30 also includes instructions for activating the aerosol generator 16. As illustrated, the controller 26 connects to the aerosol generator 16 with a cable 32 (i.e., electric cable), although in some embodiments the controller 26 may be wirelessly connected to the aerosol generator 16. The cable 32 carries a signal that activates a piezoelectric (or other) actuator inside the aerosol generator 16. As the piezoelectric actuator operates, it vibrates a vibratable member that then aerosolizes the fluid for delivery to the patient (i.e., through inhalation). The memory may therefore include instructions for controlling when the piezoelectric actuator starts, stops, vibration frequency or frequencies, etc.

The aerosol delivery system 10 increases treatment effectiveness by timing the creation of the aerosol. For example, the aerosol delivery system 10 may begin aerosolizing the medicament before the patient inhales. In this way, the aerosol delivery system 10 takes advantage of the increased airflow at the start of inhalation. This increases the medicament delivery to the patient as the inhaled air carries the medicament farther into the patient's lungs. The aerosol delivery system 10 may also aerosolize medicament as soon as inhalation is detected (e.g., for spontaneous breathing).

The aerosol delivery system 10 coordinates delivery of the medicament using one or more breath sensors 34 to determine when a patient inhales and for how long. The breath sensors 34 may include a flow sensor 36 (e.g., electrical flow sensor), radar sensor 38 (e.g., UWB radar sensor for measuring chest displacement), CO2 sensor, high-speed temperature sensor 40, acoustic sensor 40, impedance plethysmography sensor 40, respiratory inductance plethysmography sensor, pressure sensor, etc. These breath sensors 34 may communicate with the controller 26 through wired connections and/or wireless connections. In some embodiments, the aerosol delivery system 10 may use a combination of breath sensors 34 (e.g., 1, 2, 3, 4, 5) to provide redundancy and/or more accurate monitoring of the patient's breathing cycle. For example, the aerosol delivery system 10 may use a flow sensor 36 in combination with a radar sensor 38 to monitor both airflow and chest movement. In another embodiment, the aerosol delivery system 10 may use a flow sensor 36, a radar sensor 38, and plethysmography sensor 40 to monitor the breathing cycle.

As illustrated, the flow sensor 36 couples to a gas delivery conduit 42 to sense changes in airflow during inhalation (e.g., mandatory, assisted, or spontaneous breathing). In some embodiments, the flow sensor 36 may also couple to a gas return conduit 44 to detect the start and end of exhalation. And in still other embodiments, the aerosol delivery system 10 may include flow sensors 36 that couple to the gas delivery conduit 42 and the gas return conduit 44. As the controller 26 receives data from the flow sensor(s) 36, the controller 26 may monitor breathing patterns to predict when the patient is going to breath. The ability to predict when inhalation begins enables the aerosol delivery system 10 to prepare aerosolized medicament for immediate inhalation. More specifically, the aerosol delivery system 10 is able to preload fluid on a vibratable member in the aerosol generator 16 so that the fluid can be aerosolized before inhalation. Because flow detection is not a lagging indicator, the flow sensor 36 can rapidly detect unusual or spontaneous inhalation for aerosol delivery (e.g., less than 10 milliseconds from the start of inhalation).

Predicting the patient's inhalation may begin by using one or more breath and/or flow sensors 36 to tracking the patient's breathing pattern and/or a ventilation cycle (if a patient is mandatorily ventilated). The controller 26 then uses the tracked data to predict when subsequent inhalations will begin. This allows the controller 26 to direct the pump 24 to deliver fluid from the fluid source 20 to the aerosol generator 16 prior to an inhalation. The controller 26 may also signal the aerosol generator 16 to begin aerosolizing the fluid at a proper time, such as within a predetermined time period (e.g., +/−0.5 seconds) before and/or during the predicted inhalation. In this way, aerosol is ready for the patient at the start of inhalation. While the aerosol delivery system 10 is able to predict the breath cycle to produce aerosol for the patient, the aerosol delivery system 10 is also able to recognize spontaneous/irregular breathing not part of the normal pattern using the breath sensors 34. Once a spontaneous breath is recognized, the aerosol delivery system 10 may immediately pump fluid to the aerosol generator 16 for delivery to the patient.

When a patient is mandatorily ventilated (e.g., with the ventilator 14) or receives assisted ventilation, the flow sensor 36 is able to detect changes in flow as the ventilator 14 alternates between forcing air into a patient and drawing air out of the patient. The controller 26 monitors these changes in flow and then calculates when to begin aerosolizing the medicament as discussed above. In this way, the aerosol delivery system 10 can be integrated into an existing respiratory system 12 without programing or connecting the systems together. In other words, the aerosol delivery system 10 and the respiratory system 12 do not need to communicate with each other to coordinate/time aerosolization production and delivery to the patient.

It should be noted that a flow sensor 36 is more capable than a pressure sensor at detecting when a patient begins inhaling. A pressure sensor provides a lagging or delayed indicator as pressure takes time to build in an air circuit. A pressure sensor will therefore detect inhalation after the breath is over or almost over. Pressure sensors are also ineffective at determining when inhalation is complete because a pressure sensor needs a sustained inspiratory pause (i.e., plateau pressure when a patient pauses between inhaling and exhaling). Furthermore, in the event of a leak in the air circuit and/or kinks in the tubing the accuracy of pressure sensors is significantly reduced. Finally, a system that uses a pressure sensor would require a robust adaptive control algorithm to operate across mandatory, assisted, and spontaneous breathing situations because ventilator breathing creates positive pressure while spontaneous breathing creates negative pressure in the air circuit. However, in some situations a pressure sensor may be used with the aerosol delivery system 10 when the timing of aerosol production and delivery is less demanding.

Figure 2:
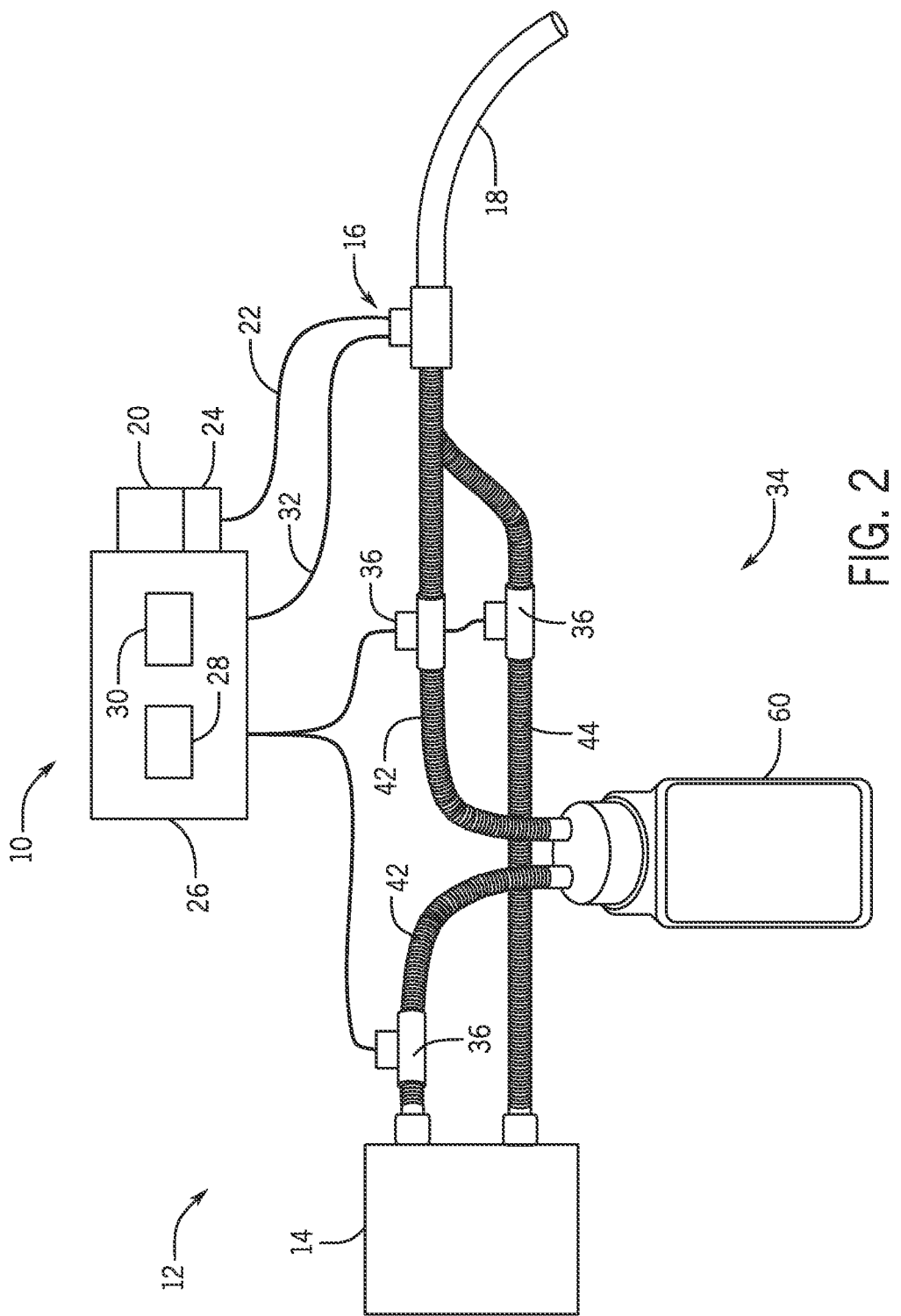
FIG. 2 is a schematic view of an embodiment of an aerosol delivery system connected to a respiratory system.

As explained above, the aerosol delivery system 10 is capable of connecting to a variety of existing systems to provide aerosolized fluid (e.g., medicament) for patient treatments without redesigning or reengineering those existing breathings systems 12 (e.g., communication). In FIG. 2, the aerosol delivery system 10 connects to a respiratory system 12 that includes a ventilator 14 and a humidifier 60. Some respiratory systems 12 may include humidifiers to moisten air before inhalation by the patient. As illustrated, the gas delivery conduit 42 couples the humidifier 60 to the ventilator 14 and to the patient. As the air passes through the humidifier 60, the air is moistened before entering the endotracheal tube 18. In other embodiments, the gas delivery conduit 42 may couple to a nasal cannula, tracheostomy tube, etc. The aerosol delivery system 10 also couples to the endotracheal tube 18 where it aerosolizes the fluid that is then carried to the patient.

Included in the aerosol delivery system 10 is a fluid source 20 (e.g., container, vial) containing medicament, surfactant, etc. The fluid source 20 fluidly couples to the aerosol generator 16 with a fluid delivery conduit 22. In operation, fluid in the fluid source 20 is pumped with a pump 24 through the fluid delivery conduit 22 to the aerosol generator 16 where the fluid is aerosolized before and/or while the patient inhales. The pump 24 is controlled with a controller 26 that controls the amount and timing of delivery to the aerosol generator 16.

The controller 26 coordinates delivery of fluid to the aerosol generator 16 and then aerosolization of the fluid by communicating with breath sensors 34. In FIG. 2, the breath sensors 34 are flow sensors 36, but other breath sensors 34 may be used alone or in combination with the flow sensor 36. As illustrated, multiple flow sensors 36 couple to the respiratory system 12, but in other embodiments a single flow sensor 36 may couple to the respiratory system 12. For example, a flow sensor 36 may couple to a gas delivery conduit 42 and a gas return conduit 44. In some embodiments, a single flow sensor 36 may couple to the respiratory system 12 upstream from the humidifier 60. Placement of the flow sensor 36 upstream from the humidifier may increase the longevity of the flow sensor 36 (e.g., electrical flow sensor 36) by blocking or reducing contact between the flow sensor 36 and moisture added by the humidifier 60, although some embodiments may feature a flow sensor 36 positioned downstream of a humidifier 60. Some embodiments may include a first flow sensor 36 upstream from the humidifier 60 and another flow sensor 36 downstream from the humidifier 60. The inclusion of two or more flow sensors 36 may provide redundancy in detecting the start and stop of inhalation by the patient and/or forced air delivery from the ventilator 14. In still another embodiment, the aerosol delivery system 10 may include one or more flow sensors 36 that couple to the gas delivery conduit 42 and one or more flow sensors 36 that couple to the gas return conduit 44. Including flow sensors 36 on the both the gas delivery conduit 42 and the gas return conduit 44 may provide redundant monitoring as well as more detailed information on when a patient begins to inhale, stops inhaling, starts to exhale, and stops exhaling. By monitoring the breath cycle, the controller 26 is able to increase the effectiveness of the medicament by timing the creation and delivery of the aerosol.

Figure 3:
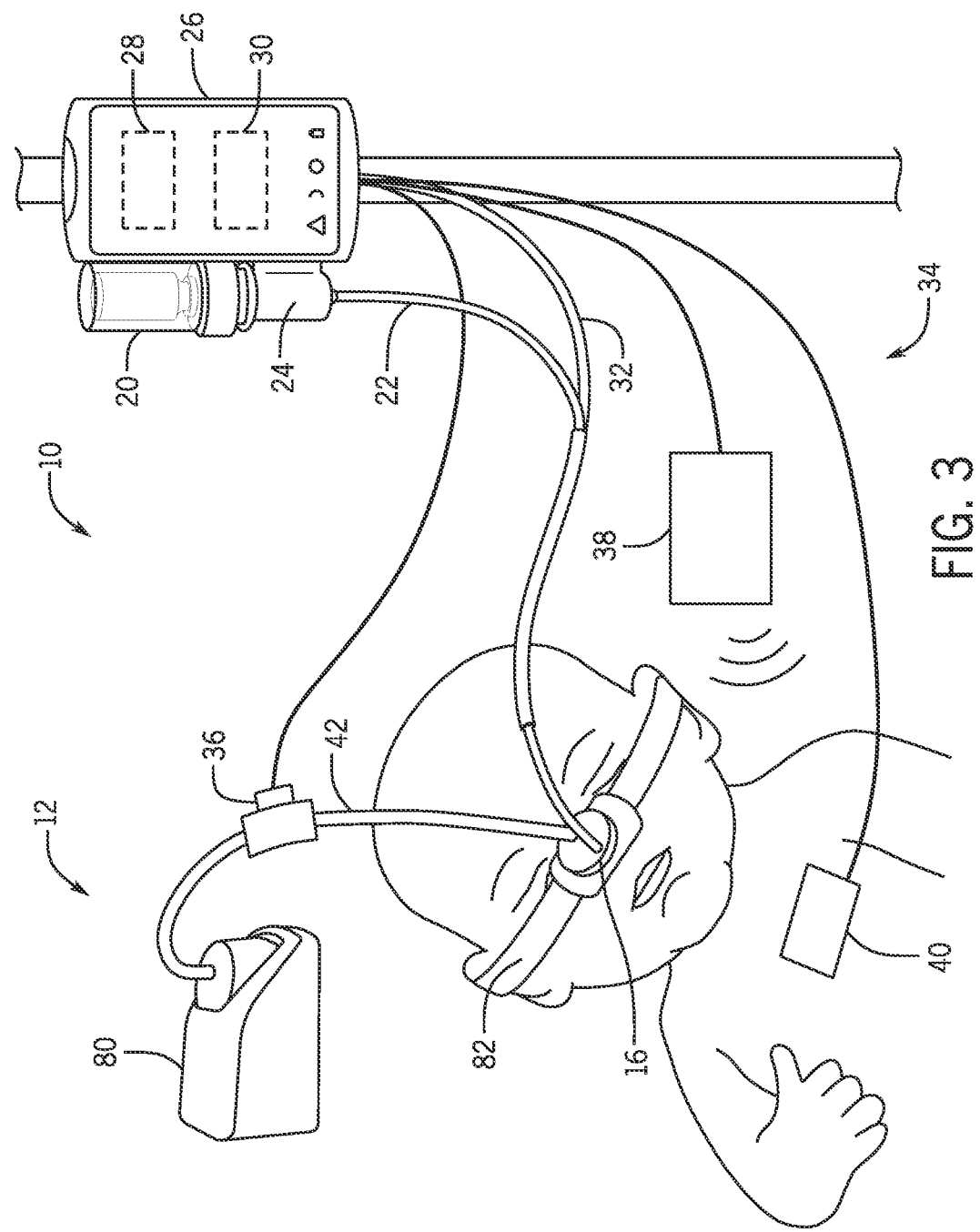
FIG. 3 is a schematic view of an embodiment of an aerosol delivery system connected to a respiratory system.

FIG. 3 is a schematic view of an embodiment of an aerosol delivery system 10 connected to a respiratory system 12 that includes a continuous positive airway pressure (CPAP) machine 80 (e.g., nCPAP). In operation, the CPAP machine 80 pumps air into a patient's throat to block the airway from collapsing. In FIG. 3, the CPAP machine 80 couples to a nasal cannula 82 with the gas delivery conduit 42. The nasal cannula 82 then directs the air into the patient through the nose. As illustrated, the aerosol delivery system 10 couples to the CPAP machine 80 with a flow sensor 36 on the gas delivery conduit 42 and to the nasal cannula 82 with the aerosol generator 16. In some embodiments, the aerosol delivery system 10 couples at or near an end of the existing respiration system prior to or at the patient interface. In this way, the aerosol delivery system 10 may couple to an existing CPAP machine 80 without redesigning or reengineering the CPAP machine 80.

As explained above, fluid is pumped from the fluid source 20 with a pump 24 through the fluid delivery conduit 22 to the aerosol generator 16. The aerosol generator 16 then aerosolizes the fluid before and/or while the patient inhales with a piezoelectric (or other) actuator inside the aerosol generator. The pump 24 is controlled with a controller 26 that times fluid delivery and the amount delivered to the aerosol generator 16. The controller 26 coordinates delivery of fluid to the aerosol generator 16 and then aerosolization of the fluid by communicating with the flow sensor 36. In some embodiments, the aerosol delivery system 10 may use another kind of breath sensor 34 and/or additional flow sensors 36 to redundantly sense a patient's breath cycle. Additional breath sensors 34 may include a radar sensor 38 (e.g., UWB radar sensor for measuring chest displacement), CO2 sensor, high-speed temperature sensor 40, acoustic sensor 40, impedance plethysmography sensor 40, respiratory inductance plethysmography sensor, etc. Including two or more breath sensors 34 may provide redundancy in detecting the start and stop of inhalation by the patient.

Figure 4:
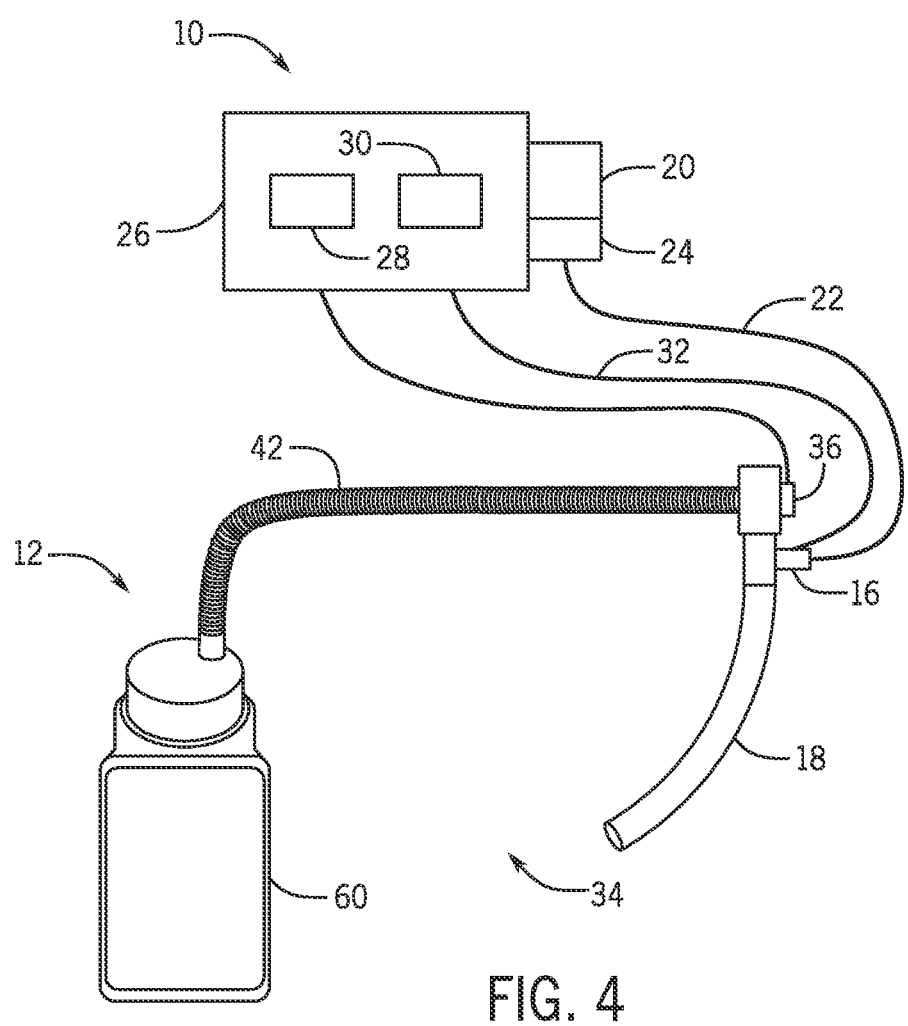
FIG. 4 is a schematic view of an embodiment of an aerosol delivery system connected to a respiratory system.

FIG. 4 is a schematic view of an embodiment of an aerosol delivery system 10 connected to a respiratory system 12 that includes a humidifier 60. The humidifier 60 adds moisture, with or without heat, to increase the humidity of the gas inhaled by the patient to avoid drying out the patient's airway. As illustrated, the humidifier 60 couples to the endotracheal tube 18 with the gas delivery conduit 42. In other embodiments, the gas delivery conduit 42 may couple the humidifier 60 to a nasal cannula, tracheostomy tubes, etc. The aerosol delivery system 10 also couples to the endotracheal tube 18 where it aerosolizes the fluid for delivery to the patient.

The aerosol delivery system 10 includes a fluid source 20 (e.g., container, vial) containing medicament, surfactant, etc. The fluid source 20 fluidly couples to the aerosol generator 16 with a fluid delivery conduit 22. In operation, fluid in the fluid source 20 is pumped with a pump 24 through the fluid delivery conduit 22 to the aerosol generator 16 where the fluid is aerosolized before and/or while the patient inhales. The pump 24 is controlled with a controller 26 that times delivery and the amount of fluid received by the aerosol generator 16. The controller 26 coordinates fluid delivery and then aerosolization of the fluid by communicating with breath sensors 34. In FIG. 4, the breath sensor 34 is a flow sensor 36. However, additional breath sensors 34 may be used alone or in combination with the flow sensor 36 (e.g., a radar sensor 38, CO2 sensor, high-speed temperature sensor 40, acoustic sensor 40, impedance plethysmography sensor 40, respiratory inductance plethysmography sensor, etc.). Monitoring inhalation and/or exhalation of the patient facilitates effective delivery of the medicament, which may reduce the amount of medicament used to treat a patient as well as the effectiveness of the aerosolized medicament.

Figure 5:
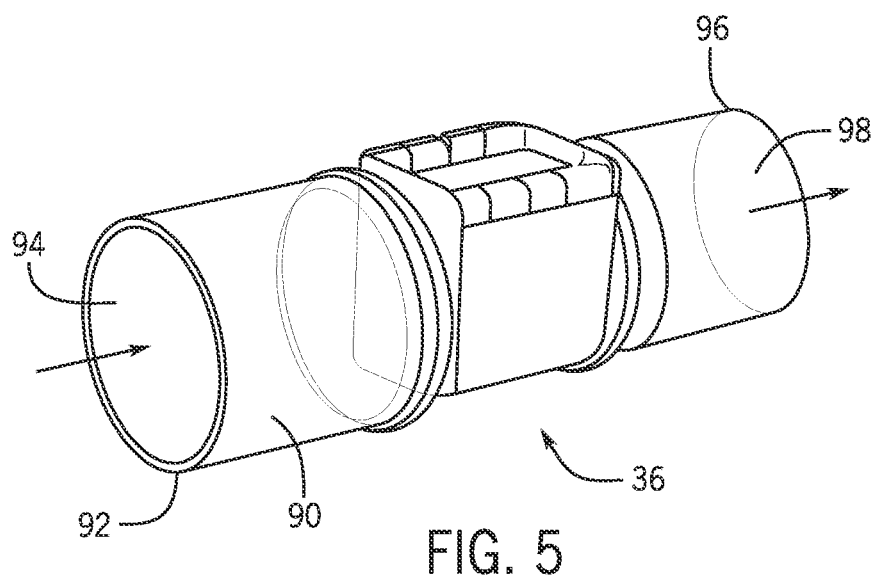
FIG. 5 is a perspective view of a conduit adapter with a fluid flow sensor.

FIG. 5 is a perspective view of a conduit adapter 90 with a flow sensor 36. As explained above, the aerosol delivery system 10 may be retrofitted to an existing respiratory system 12, which includes adding one or more breath sensors 34 to detect inhalation and/or exhalation of the patient. In some embodiments, the aerosol delivery system 10 includes one or more flow sensors 36 that couple to one or more conduits (e.g., gas delivery conduit 42, gas return conduit 44). As illustrated, the flow sensor 36 rests within a conduit adapter 90 (e.g., housing) that defines a first end 92 with an inlet 94 and a second end 96 with an outlet 98. In some embodiments, the first end 92 may couple directly to the outlet of a ventilator, CPAP machine, humidifier, etc. while the second end couples to a conduit (e.g., gas delivery conduit 42, gas return conduit 44). In another embodiment, the first end 92 and the second end 96 may couple to conduits (e.g., gas delivery conduit 42, gas return conduit 44). In this way, the flow sensor 36 may be retrofitted to an existing respiratory system 12 without reengineering or redesigning the respiratory system 12.

Figure 6:
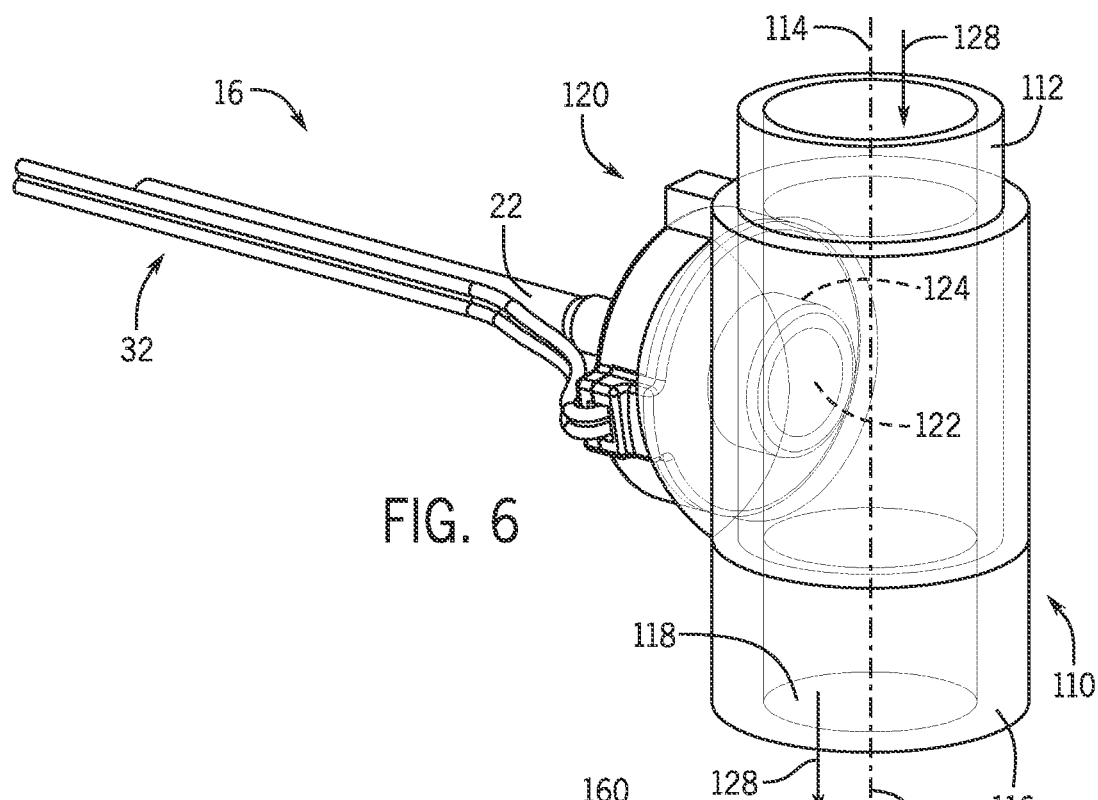
FIG. 6 is a perspective view of an embodiment of an aerosol generator coupled to a conduit connector.

FIG. 6 is a perspective view of an embodiment of an aerosol generator 16 coupled to an endotracheal/tracheostomy tube adapter 110. The adapter 110 enables the aerosol generator 16 to fluidly couple between the gas delivery conduit 42 and the endotracheal tube or tracheostomy tube 18 (seen in FIG. 1). In this position, the adapter 110 places the aerosol generator 16 closer to the patient, which increases the percentage of aerosol delivered to the patient. As illustrated, the adapter 110 includes a first end 112 with an inlet 114 that may couple to a gas delivery conduit 42 for medical treatment using a ventilator, CPAP machine, humidifier, or a combination thereof. In some embodiments, the first end 112 may not couple to anything and instead receives atmospheric air surrounding the patient. The second end 116 with the outlet 118 couples to an endotracheal tube or tracheostomy tube 18 with a press fit connection, snap fit connection, threaded connection, weld, glue, etc. to secure the aerosol generator 16 to the patient.

As illustrated, the aerosol generator 16 includes a housing 120. Within the housing 120, the aerosol generator 16 contains a vibratable member and piezoelectric actuator. In operation, the controller 26 drives the pump 24 (seen in FIGS. 1-4) to force fluid through the fluid delivery conduit 22 and into the housing 120. As explained above, the fluid delivery conduit 22 may be primed with fluid to facilitate preloading of the fluid on the vibratable member. As the fluid enters the housing 120 it spreads over some or all of the vibratable member. The controller 26 then transmits an electrical signal to the piezoelectric (or other) actuator, which then vibrates the vibratable member and aerosolizes the fluid. The aerosolized fluid then exits the housing 120 through an outlet 122 and into the tube adapter 110.

In some embodiments, the housing 120 may extend through an aperture 124 in the tube adapter 110 so that the aerosolized fluid exits the outlet 122 closer to a central axis 126 of the tube adapter 110. This may enable the carrier fluid stream 128 passing through the tube adapter 110 to capture more of the aerosol for delivery to the patient. In some embodiments, the outlet 122 of the housing 120 may be flush with or surrounds the aperture 124 in the tube adapter 110. The housing 120 may be welded, glued, snap fit, threaded, press fit, etc. to the tube adapter 110. In some embodiments, the aerosol generator housing 120 may form a fluid tight seal with the tube adapter 110 using a gasket, a weld, glue, etc. to block contaminants from being inhaled by the patient.

Figure 7:
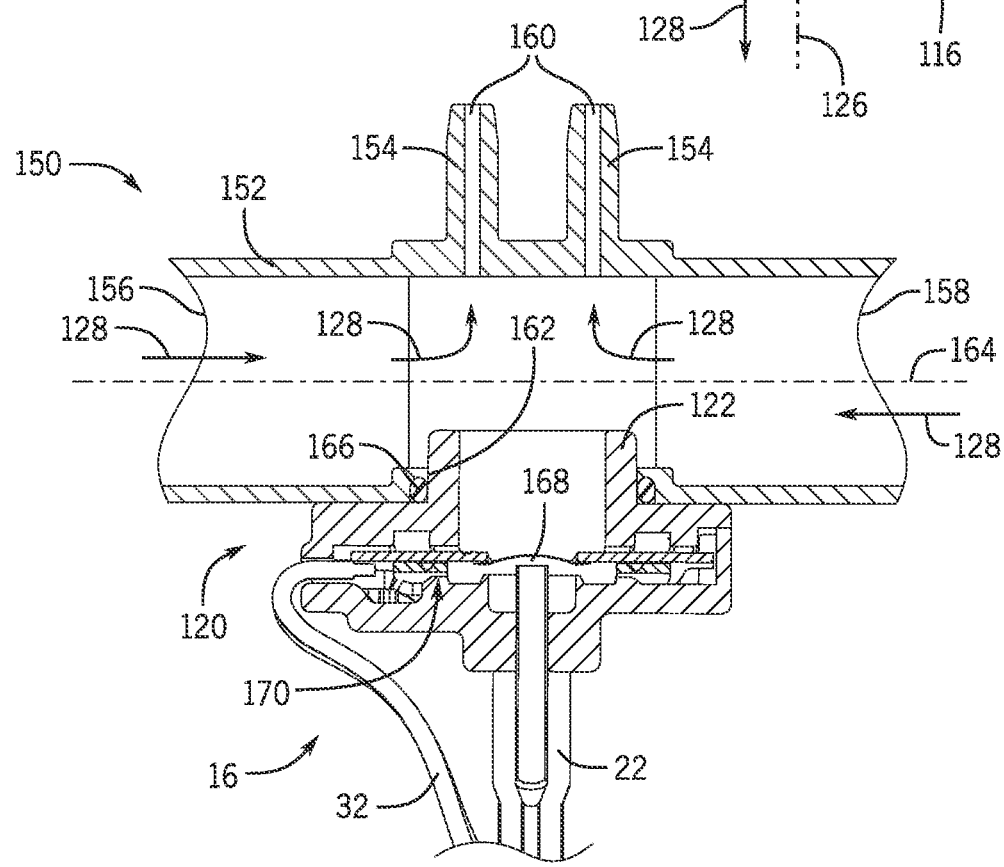
FIG. 7 is a cross-sectional view of an embodiment of an aerosol generator coupled to a nasal cannula.

FIG. 7 is a cross-sectional view of an embodiment of an aerosol generator coupled to a nasal mask or nasal cannula 150. The nasal cannula 150 includes a body 152 with nasal prongs 154 that extend away from the body 152. The nasal cannula 150 may include first and second inlets 156, 158 that feed a carrier fluid 128 to apertures 160 in the nasal prongs 154. However, some embodiments may include either inlet 156 or 158 to feed the carrier fluid 128 to the nasal prongs 154. Similar to the discussion above, the aerosol generator housing 120 may extend through the aperture 160 and into the nasal cannula 150 so that the aerosolized fluid exits the outlet 122 closer to a central axis 164. This may facilitate the flow of the aerosol to the patient as the aerosol enters closer to the center of the carrier fluid stream 128 flowing through the nasal cannula 150. In some embodiments instead of extending into the nasal cannula 150, the outlet 122 of the housing 120 may be flush with or surround the aperture 162.

The housing 120 of the aerosol generator 16 may couple to the nasal cannula 150 using a weld, glue, etc. or may couple using a snap fit connection, threaded connection, press fit connection, etc. In some embodiments, the aerosol generator housing 120 may form a fluid tight seal with the tube adapter 110 using a gasket 164, a weld, glue, etc. to block contaminants from entering the fluid stream inhaled by the patient.

As explained above, the aerosol generator 16 includes a vibratable member 168 that vibrates and aerosolizes the fluid in response to a piezoelectric actuator 170. The vibratable member 168 may be a photo-defined vibratable member as described in U.S. Patent Publication 2016/0130715 published on May 12, 2016 and which is hereby incorporated in its entirety for all purposes. The vibratable member may be made out of polymer, metal, metal alloys, etc. In operation, the vibratable member 168 is capable of producing a fine particle fraction (FPF) of 99.6% or greater with droplets/particles having a volume median diameter (VIVID) of 4 microns or less. In some embodiments, the aerosol generator 16 using the vibratable member 168 is capable of producing an FPF of 80% or greater with droplets having a VMD of 1 micron or less. An aerosol with these characteristics is easily suspended in and carried by a carrier fluid (e.g., air, O2, O2/air mixture, etc.) for effective delivery to a patient (e.g., deliver medicament to greater depths within the patient's lungs).

Figure 8:
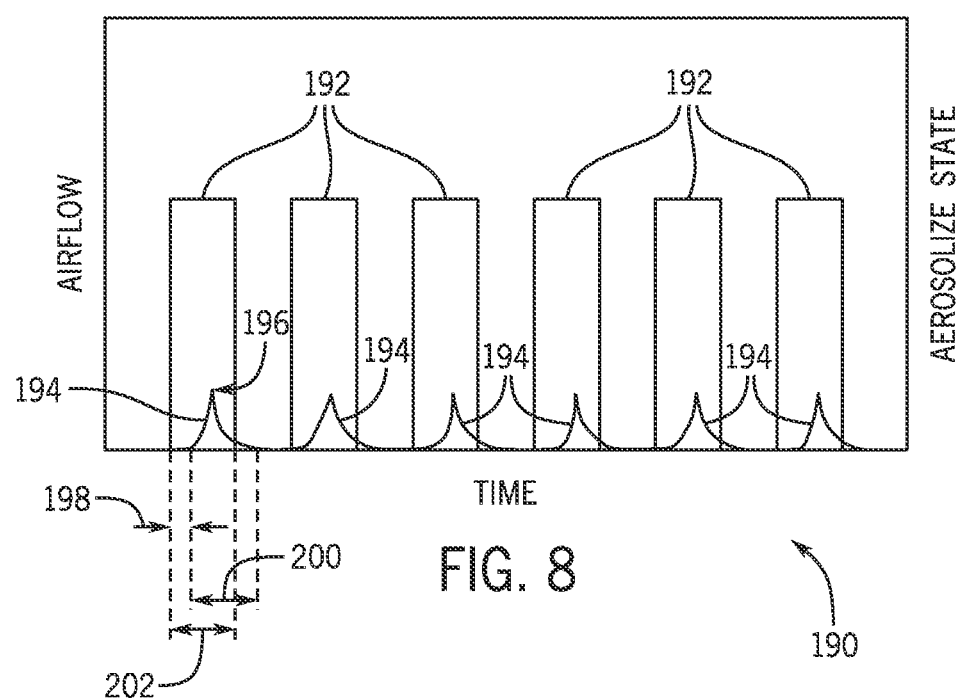
FIG. 8 is a graph illustrating when the aerosol delivery system aerosolizes a fluid with respect to when a patient breathes.

FIG. 8 is a graph 190 illustrating aerosol generation with respect to a patient's breath cycle. As explained above, the aerosol delivery system 10 includes one or more breath sensors 34 that sense when a patient inhales and exhales. After tracking the patient's breathing pattern and/or a ventilation cycle (if a patient is mandatorily ventilated) the controller 26 is able to predict when inhalation will begin. This information is then used to pump fluid to the aerosol generator 16 (e.g., preload fluid on the vibratable member 168) as well as signal the aerosol generator 16 to begin aerosolizing the fluid. In this way, aerosol is ready for the patient at the start of inhalation. While the aerosol delivery system 10 is able to predict the breath cycle to produce aerosol for the patient, the aerosol delivery system 10 is also able to recognize spontaneous/irregular breathing not part of the normal pattern using the breath sensors 34. Once a spontaneous breath is recognized, the aerosol delivery system 10 may immediately pump fluid to the aerosol generator 16 for delivery to the patient.

In graph 190, the line 192 represents aerosol production by the aerosol generator 16 and the line 194 represents airflow during inhalation. The peaks 196 represent the max airflow to the patient. As illustrated, aerosol generation begins at a time period 198 before inhalation by the patient. For example, the time period 198 may be 1-10%, 1-15%, 1-20%, 1-30%, etc. with respect to the time period 200 representing the duration of inhalation (i.e., airflow to the patient). Aerosol generation may then continue for a time period 202 before stopping near the end of inhalation. For example, aerosol generation may stop 1-10%, 1-15%, 1-20%, etc. before the end of inhalation with respect to the time period 200 representing the duration of inhalation. In this way, the aerosol delivery system 10 reduces medicament waste by stopping production of aerosol that may not be effectively delivered to the patient. In some embodiments, aerosol production may continue over the entire time period 200 representing inhalation. The aerosol generation periods 198 and 202 may also change depending on the type of treatment (e.g., medicament), patient (e.g., sex, size, age, etc.). For example, aerosol production may start and stop at different times with respect to the time period 200 (e.g., start earlier, start later, end earlier, end later). In some embodiments, aerosol production may start and stop multiple times during the time period 200. In other embodiments, the aerosol generator 16 may produce more aerosol at the start and/or before inhalation begins and then gradually reduce the amount of aerosol produced. The aerosol generator 16 may also do the opposite and gradually increase aerosol production during inhalation (e.g., as airflow to the patient increases). In still other embodiments, the aerosol generator 16 may gradually increase and gradually decrease aerosol production during inhalation (e.g., gradually increase aerosol production to peak airflow 196 and then gradually decrease aerosol production afterwards).

Figure 9:
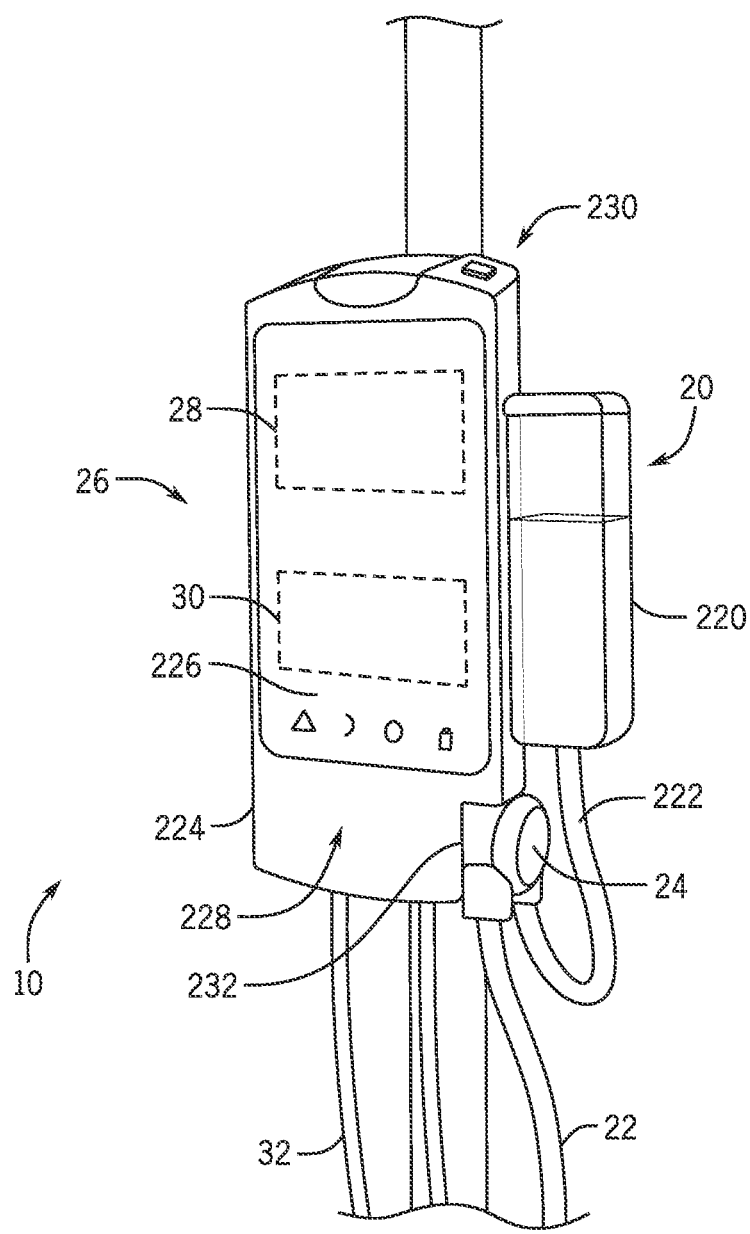
FIG. 9 is a perspective view of an embodiment of an aerosol generator system.

FIG. 9 is a perspective view of an embodiment of an aerosol delivery system 10. As illustrated, the fluid source 20 is a fluid container 220 that couples to the controller 26. The fluid container 220 couples to the pump 24 with a pump connection line 222 enabling the pump 24 to draw fluid out of the fluid source 20 when activated by the controller 26. The fluid may be medicament, surfactant, or a combination thereof. The pump 24 may be a positive displacement pump capable of discharging controlled amounts of fluid from the fluid source 20. For example, the pump 24 may be a peristaltic pump, rotary pump, reciprocating pump, plunger pump, gear pump, screw pump, progressive cavity pump, etc. In some embodiments, the pump 24 may be a non-positive displacement pump. For example, the non-positive displacement pump may be a gravity fed system such as a drip (e.g., intravenous therapy drip). In order to control the flow of fluid from the drip, the gravity fed system may include a valve. In some embodiments, the non-positive displacement pump may be a rotary vane driven pump, piezo driven pump. To increase the accuracy of fluid delivery of the non-positive displacement pumps, the system may include a liquid flow sensor, a liquid pressure sensor, and/or a volume detection sensor (e.g., wet/dry sensor, capacitive level sensor, venting pressure sensor).

As explained above, the controller 26 includes one or more processors 28 that execute instructions stored on one or more memories 30 to control operation of the pump 24 and operation of the aerosol generator 16. The controller 26 may be housed within a controller housing 224. Coupled to the controller housing 224 is a display 226 and one or more buttons 228. For example, the controller 26 may include a power button 230 for powering the controller 26 on and off as well as buttons that provide access to and navigation through one or more menus, etc. In some embodiments, the display 226 may be a touchscreen to facilitate interaction with the aerosol delivery system 10. The housing 224 may also define an indentation 232 that receives the pump 24 so that the pump 24 is aligned with a perimeter of the housing 224 or substantially aligned with the housing 224. This may increase the aesthetic look of the controller 26 as well reducing unintentional removal of the pump 24 from the controller 26 through contact with neighboring objects.

Figure 10:
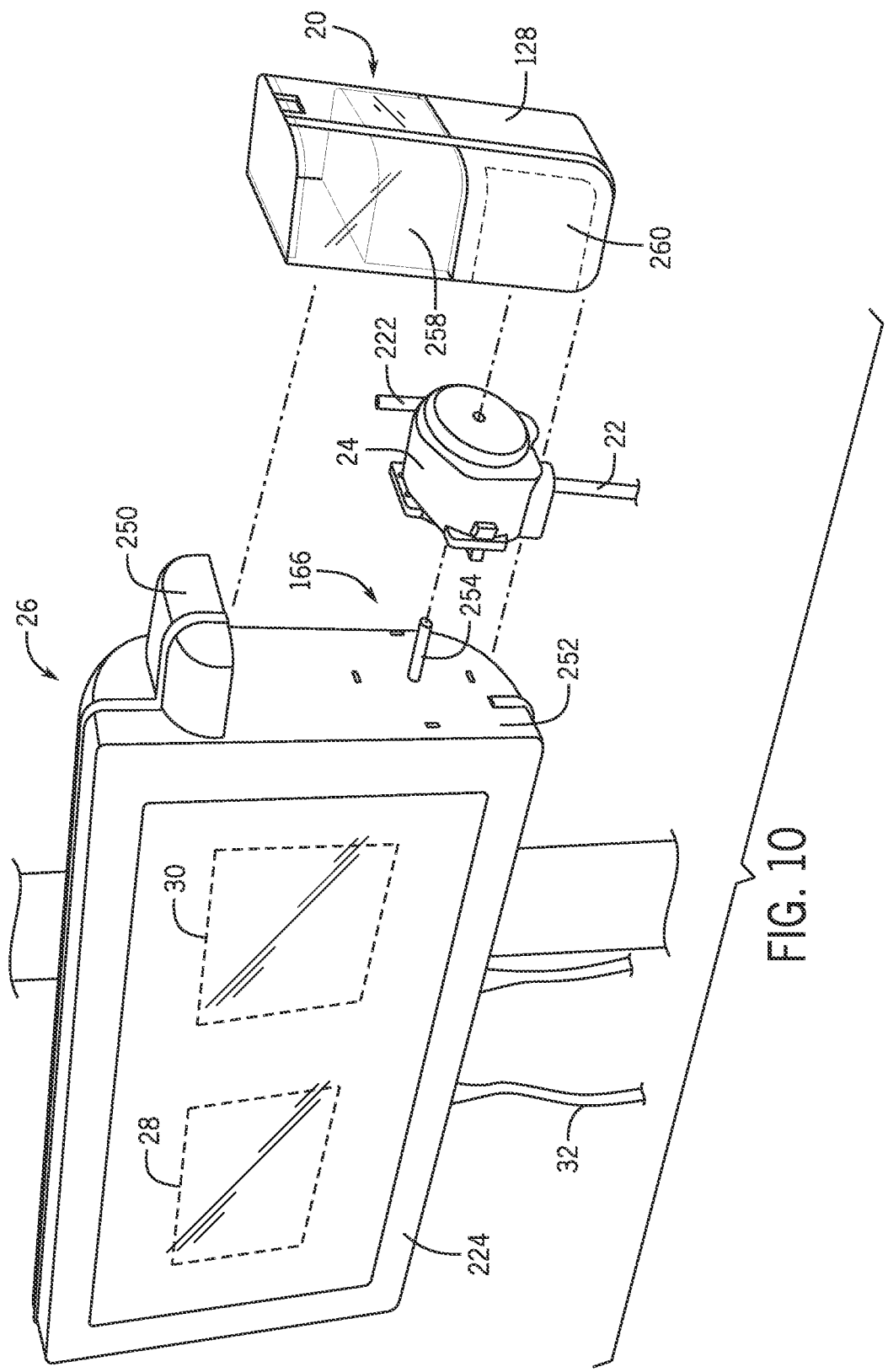
FIG. 10 is an exploded perspective view of an embodiment of an aerosol generator system.

FIG. 10 is an exploded perspective view of an embodiment of an aerosol delivery system 10. As illustrated, the controller housing 224 includes a ledge 250 that extends away from a sidewall 252. When the fluid container 220 couples to the controller housing 224, the ledge 250 protects the fluid container 220 from unintentional removal as well as from objects that users may attempt to place on top of the fluid container 220. In addition to the ledge 250, the controller 26 includes a shaft 254 that extends from the sidewall 252. The shaft couples to a motor within the controller 26. In operation, the controller 26 activates the motor, which then drives the pump 24 through the shaft 254. In some embodiments, the controller housing 224 includes multiple apertures in the sidewall 252 that facilitate coupling of the pump 24 and the fluid container 220 to the controller housing 224.

In FIG. 10, the fluid container 220 includes a fluid containing portion 258 that contains the fluid source 20 and a pump receptacle portion 260. The pump receptacle portion 260 receives the pump 24 as the fluid container 220 couples to the controller housing 224. In some embodiments, the pump 24 couples to the fluid source 20 with the pump connection line 222 within the pump receptacle portion 260. In this way, the fluid container 220 blocks or reduces unintentional disconnection of the pump connection line 222 from the fluid source 20.

Figure 11:
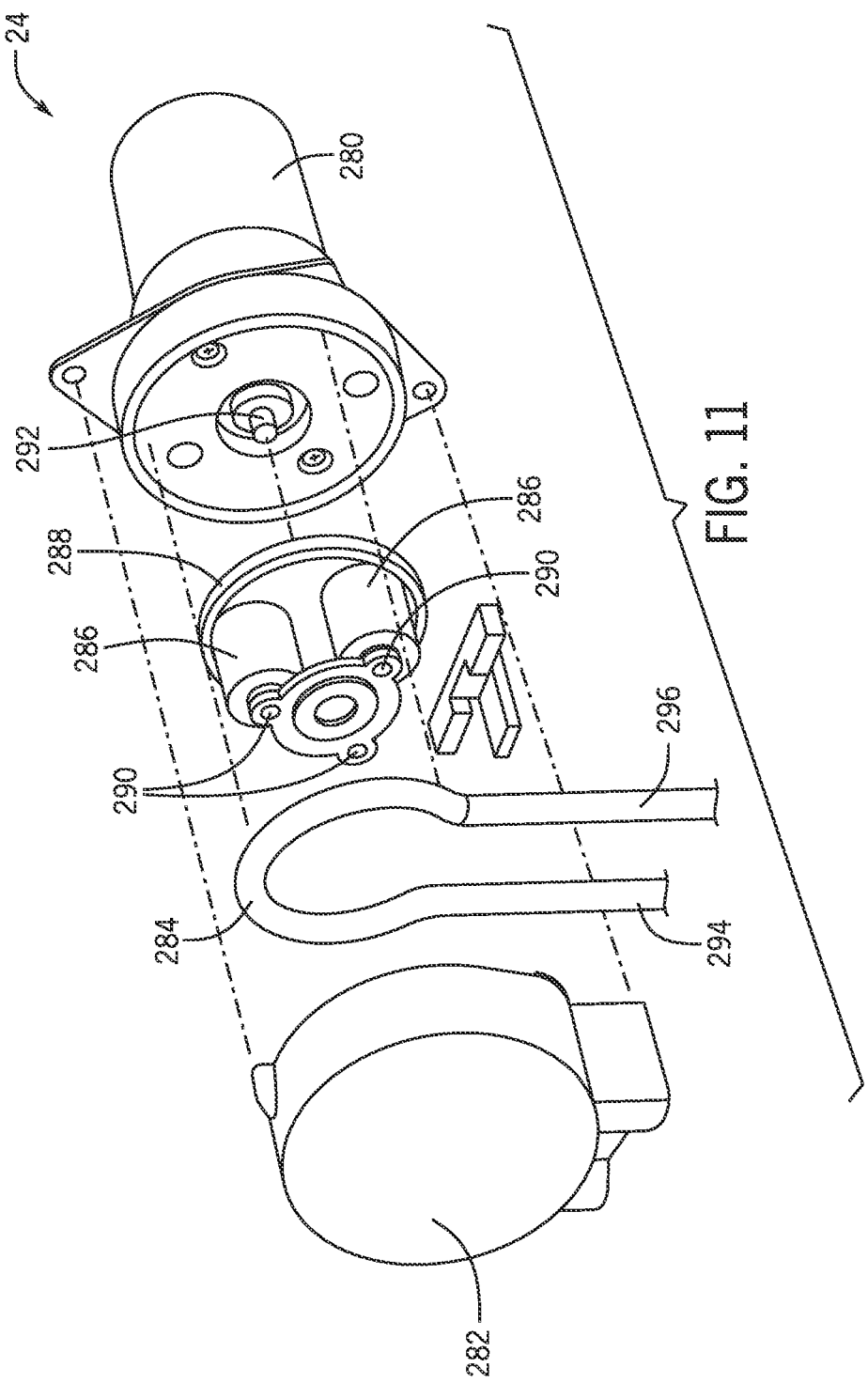
FIG. 11 is an exploded perspective view of an embodiment of a positive displacement pump.

FIG. 11 is an exploded perspective view of an embodiment of a pump 24. As explained above, the pump 24 is a positive displacement pump that enables measured release of fluid from the fluid source 20. In FIG. 11, the pump 24 is a peristaltic pump. The pump 24 includes a pump housing 280 and a cover 282 that covers a disposable tube 284 and rollers 286. The rollers 286 couple to a plate 288 with bearings 290. The bearings 290 enable the rollers 286 to rotate as the plate 288 rotates in response to movement of the shaft 292. When assembled the disposable tube 284 wraps around the rollers 286 so that the rollers 286 can compress the disposable tube 284 against an interior surface of the cover 282. As the rollers 286 rotate within the cover 282 they receive measured amounts of fluid from the fluid source 20 and then drive those measured amounts of fluid through the disposable tube 284. In some embodiments, the disposable tube 284 couples to the pump connection line 222 at an inlet 294 and to the fluid delivery conduit 22 at an outlet 296. In another embodiment, the disposable tube 284 is the pump connection line 222, which couples to the fluid delivery conduit 22. In still another embodiment, the disposable tube 284 is the fluid delivery conduit 22, which couples to the pump connection line 222 or directly to the fluid source 20.

As discussed above, embodiments of the present invention provide aerosol delivery systems that may be retrofitted onto existing respiration systems, such as ventilators, CPAP machines, humidifiers, and/or other respiration systems. For example, a user may couple a conduit adapter, such as adapter 110, between an existing artificial respiration system and a delivery lumen, such as found in a nasal cannula, facemask, mouthpiece, endotracheal tube, LMA, or a tracheostomy tube, and/or other patient interface devices. As detailed above, the conduit adapter may define an open interior and may include and/or be coupled with one or more breath sensors, such as one of (or a combination of) flow sensors, radar sensors, CO2 sensors, high-speed temperature sensors, acoustic sensors, impedance plethysmography sensors, respiratory inductance plethysmography sensors, pressure sensors, and the like, which are configured to emit a signal as a patient breathes to detect a breathing pattern. The adapter may also include and/or be coupled with an aerosol generator having an output that is in fluid communication with the open interior of the conduit adapter. The user may interface the delivery lumen with the patient's airway. Air may be to the patient using the respiratory system, with a breath cycle of the patient being detected using the breath sensor(s) as discussed in more detail above. The breath sensor(s) may communicate a signal associated with the detected breath cycle to a controller, which may use this data to predict the start of a subsequent inhalation. The controller may then cause fluid to be preloaded onto a vibratable member, such as by pumping the fluid onto the vibratable member. The vibratable member may then be vibrated by a piezoelectric actuator to aerosolize the fluid and to introduce the aerosolized fluid to the patient's airway via the open interior of the conduit adapter and the delivery lumen. In some embodiments, the process may also include coupling the pump to a fluid source and to the aerosol generator using one or more fluid lines.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of providing aerosolized fluid to a patient, comprising:
   detecting a breath cycle using at least one breath sensor of an aerosolization device;
   predicting the start of an inhalation, using the aerosolization device, by monitoring signals from the at least one breath sensor over one or more breath cycles of the patient;
   determining a duration of inhalation of the breath cycle;
   preloading fluid onto a vibratable member of the aerosolization device with a pump; and
   vibrating the vibratable member to aerosolize the fluid at a predetermined time prior to the start of a predicted inhalation, wherein the predetermined time comprises a time period between 1% and 30% before the start of the predicted inhalation with respect to the duration of inhalation.

2. The method of providing aerosolized fluid to a patient of claim 1, wherein:
   the predetermined time is within 0.5 seconds of the start of the predicted inhalation.

3. The method of providing aerosolized fluid to a patient of claim 1, further comprising:
   determining a predicted end of an inhalation; and
   stopping aerosolization of the fluid at a time period of between about 1% and 20% before the end of the predicted inhalation with respect to the duration of inhalation.

4. The method of providing aerosolized fluid to a patient of claim 1, wherein:
   the vibratable member is coupled with a piezoelectric device that vibrates the vibratable member.

5. The method of providing aerosolized fluid to a patient of claim 1, wherein:
   an amount of the fluid delivered to the vibratable member is based on one or more selected from a group comprising: a size of the patient, an age of the patient, a sex of the patient, a type of medicament, a type of additive within the fluid, and a desired amount of aerosol to be generated.

6. The method of providing aerosolized fluid to a patient of claim 1, wherein:
   vibrating the vibratable member causes the fluid to be aerosolized with a fine particle fraction (FPF) of at least 80% and with particle sizes having a volume mean diameter (VIVID) or less than about 4 microns.

7. A method of providing aerosolized fluid to a patient, comprising:
   detecting a breath cycle with a breath sensor using at least one breath sensor of an aerosolization device;
   predicting a timing of an inhalation, using the aerosolization device, by monitoring signals from the at least one breath sensor over one or more breath cycles of the patient;

determining a duration of inhalation of the breath cycle; and vibrating a vibratable member of the aerosolization device to aerosolize fluid at a predetermined time before a start of and during an inhalation cycle based on the predicted timing of the inhalation, wherein the predetermined time comprises a time period between 1% and 30% before the start of a predicted inhalation with respect to the duration of inhalation.

8. The method of providing aerosolized fluid to a patient of claim 7, further comprising:
controlling a flow of the fluid to the vibratable member based on the start of the predicted inhalation.

9. The method of providing aerosolized fluid to a patient of claim 7, further comprising:
forcing air into and withdrawing air from the patient using a respiration system that is fluidly coupled with the aerosolization device.

10. The method of providing aerosolized fluid to a patient of claim 9, wherein:
the respiration system includes one or both of a ventilator and a humidifier.

11. The method of providing aerosolized fluid to a patient of claim 9, further comprising:
moistening the air using a humidifier prior to delivering the air to the patient.

12. The method of providing aerosolized fluid to a patient of claim 7, wherein:
the at least one breath sensor comprises one or more selected from a group comprising: a flow sensor, a pressure sensor, a radar sensor, a $CO_2$ sensor, a high-speed temperature sensor, an acoustic sensor, and an impedance plethysmography sensor.

13. The method of providing aerosolized fluid to a patient of claim 7, wherein:
vibrating the vibratable member causes the fluid to be aerosolized with particle sizes having a volume mean diameter (VIVID) of less than about 4 microns.

14. A method of providing aerosolized fluid to a patient, comprising:
providing an aerosolization device, comprising:
an aerosol generator comprising a vibratable member;
a pump coupled to the aerosol device; and
at least one breath sensor;
detecting a breath cycle using the at least one breath sensor;
predicting the start of an inhalation, using the aerosolization device, by monitoring signals from the at least one breath sensor over one or more breath cycles of the patient;
determining a duration of inhalation of the breath cycle;
preloading fluid onto the vibratable member using the pump; and
vibrating the vibratable member to aerosolize the fluid at a predetermined time prior to the start of a predicted inhalation, wherein the predetermined time comprises a time period between 1% and 30% before the start of the predicted inhalation with respect to the duration of inhalation.

15. The method of providing aerosolized fluid to a patient of claim 14, wherein:
detecting the breath cycle comprises sensing a change in airflow during inhalation.

16. The method of providing aerosolized fluid to a patient of claim 14, further comprising:
detecting a spontaneous inhalation; and
vibrating the vibratable member immediately upon detecting the spontaneous inhalation.

17. The method of providing aerosolized fluid to a patient of claim 14, further comprising:
delivering the aerosolized fluid to patient through a patient interface, wherein the patient interface is selected from an endotracheal tube, a tracheostomy tube, a nasal cannula, a facemask, a mouthpiece, a laryngeal mask airway (LMA), and a nasal mask.

18. The method of providing aerosolized fluid to a patient of claim 14, wherein:
preloading the fluid onto the vibratable member begins at least 1% before the start of the predicted inhalation as measured by a duration of a predicted breath.

19. The method of providing aerosolized fluid to a patient of claim 14, further comprising:
stopping a flow of the fluid onto the vibratable member after inhalation begins, wherein the vibratable member continues to vibrate and aerosolize the fluid after the flow of fluid stops.

* * * * *